US012594046B2

(12) United States Patent
Jeong et al.

(10) Patent No.: US 12,594,046 B2
(45) Date of Patent: Apr. 7, 2026

(54) METHOD AND APPARATUS FOR ASSISTING DIAGNOSIS OF CARDIOEMBOLIC STROKE BY USING CHEST RADIOGRAPHIC IMAGES

(71) Applicant: Seoul National University Hospital, Seoul (KR)

(72) Inventors: Han-Gil Jeong, Seoul (KR); Tackeun Kim, Seongnam-Si (KR)

(73) Assignee: Seoul National University Hospital, Seoul (KR)

( * ) Notice: Subject to any disclaimer, the term of this patent is extended or adjusted under 35 U.S.C. 154(b) by 470 days.

(21) Appl. No.: 18/028,307

(22) PCT Filed: Sep. 24, 2021

(86) PCT No.: PCT/KR2021/013058
§ 371 (c)(1),
(2) Date: Oct. 12, 2023

(87) PCT Pub. No.: WO2022/065925
PCT Pub. Date: Mar. 31, 2022

(65) Prior Publication Data
US 2024/0050056 A1     Feb. 15, 2024

(30) Foreign Application Priority Data

Sep. 25, 2020    (KR) ........................ 10-2020-0125100

(51) Int. Cl.
| | |
|---|---|
| *G06T 7/00* | (2017.01) |
| *A61B 6/00* | (2006.01) |
| *A61B 6/50* | (2024.01) |

(52) U.S. Cl.
CPC ............ *A61B 6/503* (2013.01); *A61B 6/5217* (2013.01); *G06T 7/0012* (2013.01);
(Continued)

(58) Field of Classification Search
CPC ....... A61B 6/503; A61B 6/5217; A61B 6/501; G06T 7/0012; G06T 2207/10116;
(Continued)

(56) References Cited

U.S. PATENT DOCUMENTS

2005/0130230 A1*   6/2005  Davalos ................. G16B 20/20
                                                    435/7.1
2019/0357869 A1*  11/2019  Madabhushi .......... G16H 50/30
(Continued)

FOREIGN PATENT DOCUMENTS

JP        2008-525126 A      7/2008
KR      20180040287 A        4/2018
(Continued)

OTHER PUBLICATIONS

Jin Hur et al., "Cardioembolic Stroke: Dual-Energy Cardiac CT for Differentiation of Left Atrial Appendage Thrombus and Circulatory Stasis," Radiology, 2012, vol. 263, No. 3, pp. 688-695.

*Primary Examiner* — Van D Huynh
(74) *Attorney, Agent, or Firm* — Jackson Walker LLP

(57)     ABSTRACT

Embodiments relate to a method for assisting the diagnosis of cardioembolic stroke, in which the method is performed by a processor and is to assist the diagnosis of cardioembolic stroke by using chest radiographic images, the method comprising the steps of: acquiring chest radiographic images to be classified of a subject; and acquiring cardioembolic stroke diagnosis auxiliary information from the chest radiographic images to be classified of the subject, by using a neural network model, wherein the neural network model is configured to extract features from the chest radiographic images to be classified of the subject, and determine, based on the extracted features, whether the subject belongs to a group indicative of having cardioembolic stroke.

13 Claims, 13 Drawing Sheets

(52) U.S. Cl.
CPC .............. *G06T 2207/10116* (2013.01); *G06T 2207/20081* (2013.01); *G06T 2207/20084* (2013.01)

(58) Field of Classification Search
CPC . G06T 2207/20081; G06T 2207/20084; G06T 7/00; G16H 30/40; G16H 50/20
See application file for complete search history.

(56) References Cited

U.S. PATENT DOCUMENTS

| | | | |
|---|---|---|---|
| 2020/0104990 A1* | 4/2020 | Kimura ................. | G16H 30/40 |
| 2021/0093258 A1* | 4/2021 | Kalafut ................. | A61B 6/032 |
| 2021/0353203 A1* | 11/2021 | Burman ................. | G16H 50/30 |
| 2022/0012879 A1* | 1/2022 | De Poly .............. | A61B 5/0066 |
| 2022/0351854 A1* | 11/2022 | Li ........................ | G06N 3/0464 |
| 2022/0395244 A1* | 12/2022 | Taubmann ............. | A61B 6/037 |
| 2023/0289595 A1* | 9/2023 | Khosousi ............. | A61B 5/7275 |
| 2025/0014183 A1* | 1/2025 | Park ..................... | G06T 7/0012 |

FOREIGN PATENT DOCUMENTS

| | | | |
|---|---|---|---|
| KR | 101874348 | B1 | 7/2018 |
| KR | 101992057 | B1 | 6/2019 |
| KR | 102097742 | B1 | 4/2020 |
| KR | 102097743 | B1 | 4/2020 |
| KR | 20200069209 | A | 6/2020 |

* cited by examiner $$Class = \begin{cases} 1 \ if \ O^l > \Upsilon \\ 0 \ otherwise \end{cases}$$

FIG. 5

| | All patients (n=4064) | Cardioembolic stroke (n=1188) | Non-cardioembolic stroke (n=2876) | P-value |
|---|---|---|---|---|
| Demographic information | | | | |
|   Male sex | 2,478 (61.0%) | 678 (57.1%) | 1,800 (62.6%) | <0.01 |
|   Age, years | 68.7 ± 12.6 | 71.9 ± 12.0 | 67.4 ± 12.6 | <0.01 |
|   Premorbid mRS score, 0-1 | 3,641 (89.6%) | 1,028 (86.5%) | 2,613 (90.9%) | <0.01 |
| Stroke information | | | | |
|   Onset to arrival, hours | 16.5 [4.5–57.4] | 7.6 [2.0–25.2] | 21.8 [7.1–66.8] | <0.01 |
|   NIHSS score at arrival | 3 [1–7] | 5 [2–15] | 3 [1–6] | <0.01 |
|   Systolic BP, mmHg | 155.2 ± 35.4 | 151.1 ± 36.0 | 156.9 ± 35.0 | <0.01 |
|   Diastolic BP, mmHg | 84.1 ± 30.0 | 81.2 ± 31.4 | 85.4 ± 29.3 | <0.01 |
|   Hyperacute treatment | | | | |
|     IV thrombolysis | 386 (9.5%) | 209 (17.6%) | 177 (6.2%) | <0.01 |
|     Endovascular therapy | 473 (11.6%) | 313 (26.3%) | 160 (5.6%) | <0.01 |
| Risk factors | | | | |
|   Hypertension | 2,868 (70.6%) | 864 (72.7%) | 2,004 (69.7%) | 0.045 |
|   Diabetes | 1,367 (33.6%) | 338 (28.5%) | 1,029 (35.8%) | <0.01 |
|   Dyslipidemia | 1,476 (36.3%) | 403 (33.9%) | 1,073 (37.3%) | 0.03 |
|   Current smoker | 914 (22.5%) | 166 (14.0%) | 748 (26.0%) | <0.01 |
|   Atrial fibrillation | 919 (22.6%) | 901 (75.8%) | 18 (0.6%) | <0.01 |
| Laboratory information | | | | |
|   Hemoglobin, g/dL | 13.7 ± 2.0 | 13.6 ± 2.1 | 13.8 ± 2.0 | <0.01 |
|   Leukocyte count, 10³ | 8,098 ± 3024 | 8,350 ± 3330 | 7,993 ± 2882 | <0.01 |
|   Glucose, mg/dL | 139.2 ± 58.7 | 134.0 ± 50.6 | 141.3 ± 61.6 | <0.01 |
|   HbA1c, % | 6.3 ± 1.3 | 6.1 ± 1.0 | 6.4 ± 1.4 | <0.01 |
|   Total cholesterol, mg/dL | 167.9 ± 41.1 | 159.7 ± 35.8 | 171.2 ± 42.7 | <0.01 |
|   LDL cholesterol, mg/dL | 99.1 ± 32.0 | 92.7 ± 28.0 | 101.8 ± 33.1 | <0.01 |
| Outcomes | | | | |
|   mRS 0–2 at 3 months | 2,731 (67.2%) | 682 (57.4%) | 2,049 (71.2%) | <0.01 |
|   Mortality at 3 months | 167 (4.1%) | 98 (8.2%) | 69 (2.4%) | <0.01 |

FIG. 6

| | Echocardiography | | |
| | Yes (n=650) | No (n=159) | P-value |
|---|---|---|---|
| Cardioembolic stroke | 194 (29.8%) | 35 (22.0%) | 0.06 |
| Demographic information | | | |
|   Male sex | 397 (61.1%) | 93 (58.5%) | 0.61 |
|   Age, years | 68.3 ± 12.6 | 69.7 ± 12.8 | 0.23 |
|   Premorbid mRS score, 0~1 | 585 (90.0%) | 142 (89.3%) | 0.91 |
| Stroke information | | | |
|   Onset to arrival, hours | 15.5 [5.6~48.7] | 20.4 [6.1~84.9] | 0.03 |
|   NIHSS score at arrival | 3 [1~8] | 3 [1~6] | 0.16 |
|   Systolic BP, mmHg | 153.0 ± 26.4 | 150.2 ± 25.8 | 0.04 |
|   Diastolic BP, mmHg | 83.5 ± 16.4 | 81.2 ± 15.5 | 0.12 |
|   Hyperacute treatment | | | |
|     IV thrombolysis | 56 (8.6%) | 11 (6.9%) | 0.59 |
|     Endovascular therapy | 79 (12.2%) | 15 (9.4%) | 0.41 |
| Risk factors | | | |
|   Hypertension | 459 (70.6%) | 105 (66.0%) | 0.30 |
|   Diabetes | 208 (32.0%) | 56 (35.2%) | 0.50 |
|   Dyslipidemia | 212 (32.6%) | 65 (40.9%) | 0.06 |
|   Current smoker | 145 (22.3%) | 31 (19.5%) | 0.51 |
|   Atrial fibrillation | 153 (23.5%) | 29 (18.2%) | 0.18 |
| Laboratory information | | | |
|   Hemoglobin, g/dL | 13.8 ± 2.1 | 13.3 ± 2.2 | <0.01 |
|   Leukocyte count, 10⁹ | 8,042 ± 2,782 | 8,186 ± 3,394 | 0.62 |
|   Glucose, mg/dL | 139.6 ± 59.8 | 138.6 ± 52.3 | 0.83 |
|   HbA1c, % | 6.2 ± 1.2 | 6.3 ± 1.3 | 0.45 |
|   Total cholesterol, mg/dL | 169.0 ± 38.5 | 158.1 ± 39.4 | <0.01 |
|   LDL cholesterol, mg/dL | 100.0 ± 30.9 | 93.7 ± 32.0 | 0.02 |
| Outcomes | | | |
|   mRS 0~2 at 3 months | 452 (69.5%) | 102 (64.2%) | 0.22 |
|   Mortality at 3 months | 26 (4.0%) | 15 (9.4%) | 0.01 |

FIG. 7

| Variables | Total (n=650) | Predicted CE (n=163) | Predicted Non-CE (n=487) | Ratio* | P-value |
|---|---|---|---|---|---|
| Ejection fraction, % | 61.1 ± 8.7 | 56.8 ± 11.9 | 62.5 ± 6.9 | 0.91 | <0.01 |
| E/e' | 12.3 ± 6.2 | 15.9 ± 9.0 | 11.1 ± 4.2 | 1.44 | <0.01 |
| LA AP diameter, mm | 38.2 ± 7.1 | 43.6 ± 8.0 | 36.4 ± 5.8 | 1.20 | <0.01 |
| LA volume, ml | 70.7 ± 33.0 | 102.9 ± 41.6 | 59.8 ± 20.1 | 1.72 | <0.01 |
| LA volume index, ml/m² | 43.2 ± 20.3 | 62.4 ± 25.7 | 35.3 ± 12.0 | 1.77 | <0.01 |
| LV end-diastolic diameter, mm | 45.5 ± 5.6 | 47.2 ± 6.5 | 44.9 ± 5.1 | 1.05 | <0.01 |
| LV end-diastolic volume, ml | 74.9 ± 25.0 | 78.0 ± 33.9 | 73.9 ± 21.2 | 1.06 | 0.14 |
| LV end-systolic diameter, mm | 29.3 ± 6.1 | 32.0 ± 7.6 | 28.4 ± 5.2 | 1.13 | <0.01 |
| LV end-systolic volume, ml | 30.1 ± 17.5 | 35.6 ± 26.1 | 28.2 ± 13.0 | 1.26 | <0.01 |
| LV mass, g | 166.4 ± 49.6 | 181.1 ± 58.9 | 161.5 ± 45.1 | 1.12 | <0.01 |
| LV mass index, g/m² | 98.5 ± 27.2 | 109.1 ± 32.8 | 95.0 ± 24.1 | 1.15 | <0.01 |
| Any wall motion abnormality | 64 (9.9%) | 31 (19.1%) | 33 (6.8%) | 2.81 | <0.01 |
| Aortic regurgitation** | 13 (2.0%) | 6 (3.7%) | 7 (1.4%) | 2.56 | 0.15 |
| Aortic stenosis** | 7 (1.1%) | 4 (2.5%) | 3 (0.6%) | 3.98 | 0.13 |
| Mitral regurgitation** | 5 (0.8%) | 4 (2.5%) | 1 (0.2%) | 12.00 | 0.02 |
| Mitral stenosis** | 3 (0.5%) | 3 (1.8%) | 0 (0%) | N/A | 0.02 |
| Tricuspid regurgitation** | 21 (3.2%) | 15 (9.2%) | 6 (1.2%) | 7.47 | <0.01 |

FIG. 8

| Variables | Positive (predicted as cardioembolic stroke) | | Negative (predicted as non-cardioembolic stroke) | | P-value** |
| --- | --- | --- | --- | --- | --- |
| | TP (n=125) | FP (n=38) | FN (n=69) | TN (n=418) | |
| Ejection fraction, % | 56.3±12.3 | 58.6±10.2 | 60.4±9.9 | 62.8±8.2 | <0.01 |
| E/e' | 16.3±9.6 | 14.8±7.1 | 11.6±5.3 | 11.0±4.0 | <0.01 |
| LA AP diameter, mm | 45.2±7.6 | 38.2±6.9 | 39.6±6.5 | 35.9±5.5 | <0.01 |
| LA volume, ml | 110.5±41.9 | 74.5±25.3 | 72.3±25.6 | 57.7±18.3 | <0.01 |
| LA volume index, g/m² | 66.9±25.9 | 45.6±16.1 | 42.1±14.8 | 34.2±11.1 | <0.01 |
| LV end-diastolic diameter, mm | 47.3±6.6 | 46.6±6.2 | 45.5±5.9 | 44.9±5.0 | <0.01 |
| LV end-diastolic volume, ml | 76.5±35.7 | 83.2±26.8 | 75.0±27.9 | 73.7±19.9 | 0.13 |
| LV end-systolic diameter, mm | 32.4±7.9 | 30.6±6.4 | 30.1±5.9 | 28.2±5.0 | <0.01 |
| LV end-systolic volume, ml | 35.5±28.1 | 35.6±18.5 | 31.1±22.0 | 27.8±10.9 | <0.01 |
| LV mass, g | 179.3±56.5 | 187.1±66.7 | 162.7±50.5 | 161.3±44.2 | <0.01 |
| LV mass index, g/m² | 107.6±30.8 | 113.9±38.7 | 94.2±26.5 | 95.2±23.8 | <0.01 |
| Any wall motion abnormality | 20 (16.1%) | 11 (28.9%) | 6 (8.7%) | 27 (6.5%) | <0.01 |
| Aortic regurgitation* | 4 (3.2%) | 2 (5.3%) | 0 (0%) | 7 (1.7%) | 0.20 |
| Aortic stenosis* | 3 (2.4%) | 1 (2.6%) | 1 (1.4%) | 2 (0.5%) | 0.23 |
| Mitral regurgitation* | 4 (3.2%) | 0 (0%) | 1 (1.4%) | 0 (0%) | <0.01 |
| Mitral stenosis* | 3 (2.4%) | 0 (0%) | 0 (0%) | 0 (0%) | <0.01 |
| Tricuspid regurgitation* | 13 (10.4%) | 2 (5.3%) | 5 (7.2%) | 1 (0.2%) | <0.01 |

FIG. 9

| | Cardioembolic stroke (n=209) | | |
| | Predicted CE (n=132) | Predicted non-CE (n=77) | P-value |
|---|---|---|---|
| Risk of cardioembolism | | | <0.01 |
| High risk sources | 147 (73.5%) | 53 (26.5%) | |
| Medium risk sources | 5 (17.2%) | 24 (82.8%) | |
| High risk sources | | | |
| Atrial fibrillation/flutter | 137 (75.3%) | 45 (24.7%) | <0.01 |
| Left ventricular thrombus | 1 (33.3%) | 2 (66.7%) | 0.22 |
| Mechanical prosthetic valve | 1 (25%) | 3 (75%) | 0.08 |
| Atrial myxoma | 1 (50%) | 1 (50%) | 0.62 |
| Dilated cardiomyopathy | 1 (50%) | 1 (50%) | 0.62 |
| Infective endocarditis | 2 (100%) | 0 (0%) | 0.31 |
| Recent myocardial infarct | 1 (50%) | 1 (50%) | 0.62 |
| Akinetic left ventricular segments | 1 (100%) | 0 (0%) | 0.48 |
| Sick sinus syndrome | 1 (100%) | 0 (0%) | 0.48 |
| Other cause* | 1 (100%) | 0 (0%) | 0.48 |
| Medium risk sources | | | |
| Patent foramen ovale | 2 (9.1%) | 20 (90.9%) | <0.01 |
| Left atrial turbulence (smoke) | 1 (25%) | 3 (75%) | 0.08 |
| Hypokinetic left ventricular segment | 1 (50%) | 1 (50%) | 0.62 |
| Congestive heart failure | 1 (100%) | 0 (0%) | 0.48 |

| Metric | Internal test set | External test set |
|---|---|---|
| AUROC | 0.86 (0.83 – 0.89) | 0.82 (0.79 – 0.85) |
| Sensitivity | 0.66 (0.60 – 0.72) | 0.78 (0.72 – 0.83) |
| Specificity | 0.82 (0.69 – 0.94) | 0.73 (0.69 – 0.76) |
| Accuracy | 0.84 (0.82 – 0.87) | 0.74 (0.71 – 0.77) |

True negative

False negative

METHOD AND APPARATUS FOR ASSISTING DIAGNOSIS OF CARDIOEMBOLIC STROKE BY USING CHEST RADIOGRAPHIC IMAGES

TECHNICAL FIELD

The present invention relates to a method and an apparatus for assisting diagnosis of cardioembolic stroke, using chest radiographic images.

BACKGROUND

About 25% of strokes are caused by heart embolism, which is called cardioembolic stroke. Thus, it is very important to diagnose the cardioembolic stroke since it requires different diagnostic strategies, but many diagnostic tests are needed and the cause of about 20-30% of strokes cannot be identified with the tests during hospitalization. That is, there has been a limitation on the diagnosis of cardioembolic stroke even with many expensive tests required to diagnose the cardioembolic stroke.

DETAILED DESCRIPTION OF THE INVENTION

Technical Problem

Embodiments of the present invention do not require many expensive tests to diagnose cardioembolic stroke but provide an apparatus and a method for diagnosis of cardioembolic stroke using deep learning technology and chest radiographic images which can be obtained through simple tests.

Technical Solution

According to embodiments of the present invention, there is provided a method for assisting diagnosis of cardioembolic stroke comprising acquiring chest radiographic images to be classified of a subject; and generating, by using a neural network model, cardioembolic stroke diagnosis auxiliary information from the chest radiographic images to be classified of the subject and determining, based on the generated auxiliary information, whether the subject belongs to a group indicative of having cardioembolic stroke.

In addition, according to embodiments of the present invention, there is provided an apparatus for assisting diagnosis of cardioembolic stroke comprising: an acquisition unit for acquiring chest radiographic images to be classified of a subject; and a determination unit for generating, by using a neural network model, cardioembolic stroke diagnosis auxiliary information from the chest radiographic images to be classified of the subject and determining, based on the generated auxiliary information, whether the subject belongs to a group indicative of having cardioembolic stroke.

Advantageous Effects

The chest radiograph is the most frequently photographed image in medical history. It is inexpensive and easy to obtain information about the thoracic structure from chest radiographs. Because the changes that occur in the heart are reflected a lot in chest X-rays, the chest radiographs can give various information related to the cause of stroke.

According to an aspect of the present invention, the method for assisting diagnosis of cardioembolic stroke using chest radiographic images has the advantage of being able to help in diagnosis of cardioembolic stroke by using only chest radiographic images which are inexpensive and easy to be taken immediately upon arrival at any hospital.

Deep neural network technology exhibits very powerful performance in finding features that are difficult to extract or classify easily with the human eye. The present invention, using a convolutional neural network (CNN) which is a part of deep learning technology, diagnoses cardioembolic stroke using chest radiographic images and it is of great help in diagnosis of cardioembolic stroke with a relatively simple chest X-ray.

The effects of the present invention are not limited to the effects mentioned above, and other effects not mentioned will be clearly understood by those skilled in the art from the description of the claims.

BRIEF DESCRIPTION OF THE DRAWINGS

To describe the technical solution of embodiments of the present invention or the prior art more clearly, the drawings required in the description of the embodiments are briefly introduced below. It should be understood that the drawings below are for the purpose of explaining the embodiments of the present description and not for the purpose of limitation. In addition, some elements to which various modifications such as exaggeration and omission are applied may be shown in the drawings below for clarity of explanation.

FIG. 5 is a table showing baseline characteristics of the study population according to an embodiment of the present invention.

FIG. 6 is a table showing population characteristics of a data set for learning based on echocardiography according to an embodiment of the present invention.

FIG. 7 is a table showing a comparison between results predicted by ASTRO-X, which is a model according to an embodiment of the present invention, and echocardiographic results.

FIG. 8 is a table showing true positive (TP), false positive (FP), false negative (FN) and true negative (TN) indicating the correlation between the results of ASTRO-X and the results of echocardiography of FIG. 7.

FIG. 9 is a table comparing estimated causes of cardioembolic stroke according to predictions of ASTRO-X in FIG. 7.

DETAILED DESCRIPTION OF EMBODIMENTS

Figure 1:
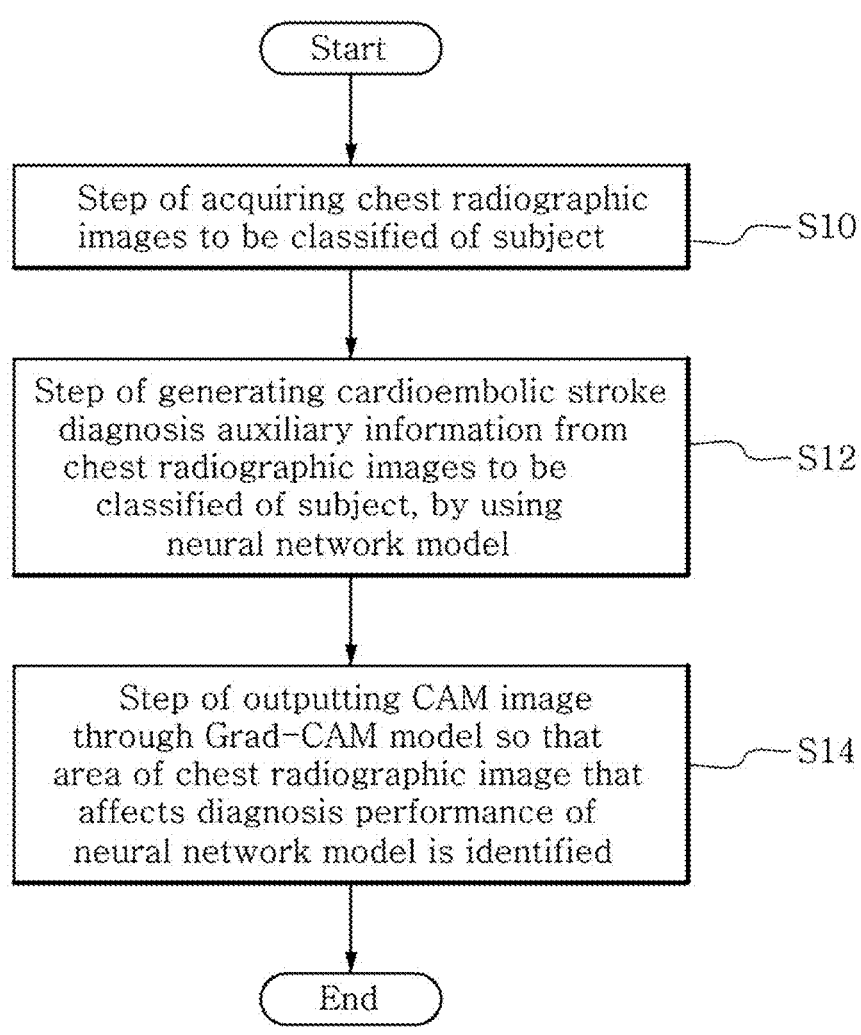
FIG. 1 is a flowchart of a method using a neural network model for assisting diagnosis of cardioembolic stroke using chest radiographic images according to an embodiment of the present invention.

Hereinafter, some embodiments of the present invention are described in detail with reference to drawings. In adding reference numerals to the components of each drawing, the same numerals could be given to the same components as much as possible, even when they are displayed on different drawings. In addition, in describing the present embodiments, if it is determined that a detailed description of a related known configuration or function may obscure the present technical idea, the detailed description could be omitted. When "include", "have", "consist of", etc. mentioned in this description are used, other parts may be added unless "only" is used. When a component is expressed as singular, it may include the case of being plural unless otherwise explicitly stated.

In addition, in describing the components of the present invention, terms such as first, second, A, B, (a), (b) may be used. These terms are only used to distinguish the component from other components, and the nature, sequence, order, or number of the corresponding component is not limited by the terms.

In the description of the positional relationship of components, when it is described that two or more components are "linked", "coupled" or "connected", the two or more components may be directly "linked", "coupled" or "connected". However, it should be understood that other components may be further "interposed" such that two or more components are "linked", "coupled" or "connected", where the other components may be included in one or more of the two or more components that are "connected", "coupled" or "connected".

In the description of the temporal relationship related to components, operation methods or production methods, when a chronological relationship is described using, for example, "after", "following", "subsequent to", "before", etc., it may also include non-continuous cases unless "immediately" or "directly" is stated. If a numerical value or its corresponding information (e.g. level, etc.) for a component is mentioned, even if there is no separate explicit description, it may be interpreted as including the error range that may occur due to various factors.

Throughout the detailed description and claims of the present invention, 'training' or 'learning' refers to performing machine learning through procedural computing and is not intended to refer to mental operations such as human educational activities, which will be understood by those skilled in the art.

Hereinafter, embodiments of the present invention will be described in detail with reference to the drawings.

FIG. 1 is a flowchart of a method using a neural network model for assisting diagnosis of cardioembolic stroke using chest radiographic images according to an embodiment of the present invention.

Referring to FIG. 1, a method using a neural network model for assisting diagnosis of cardioembolic stroke using chest radiographic images includes a step S10 of acquiring chest radiographic images of a subject and a step S12 of generating cardioembolic stroke auxiliary information from chest radiographic images to be classified of the subject using a neural network model.

In the step S10 of acquiring chest radiographic images, human mid-thoracic X-ray medical images may be input. A component that takes a chest X-ray of a subject may be implemented as various imaging devices that may be used in the art. In an embodiment, in the step S10 of acquiring chest radiographic images, medical images of the chest of the human body may be captured, and chest radiographic images may be received from a medical imaging system that captures medical images of the chest of the human body and stores the captured images. The received chest radiographic images are classified by the neural network model 20 in the step S12.

Figure 2:
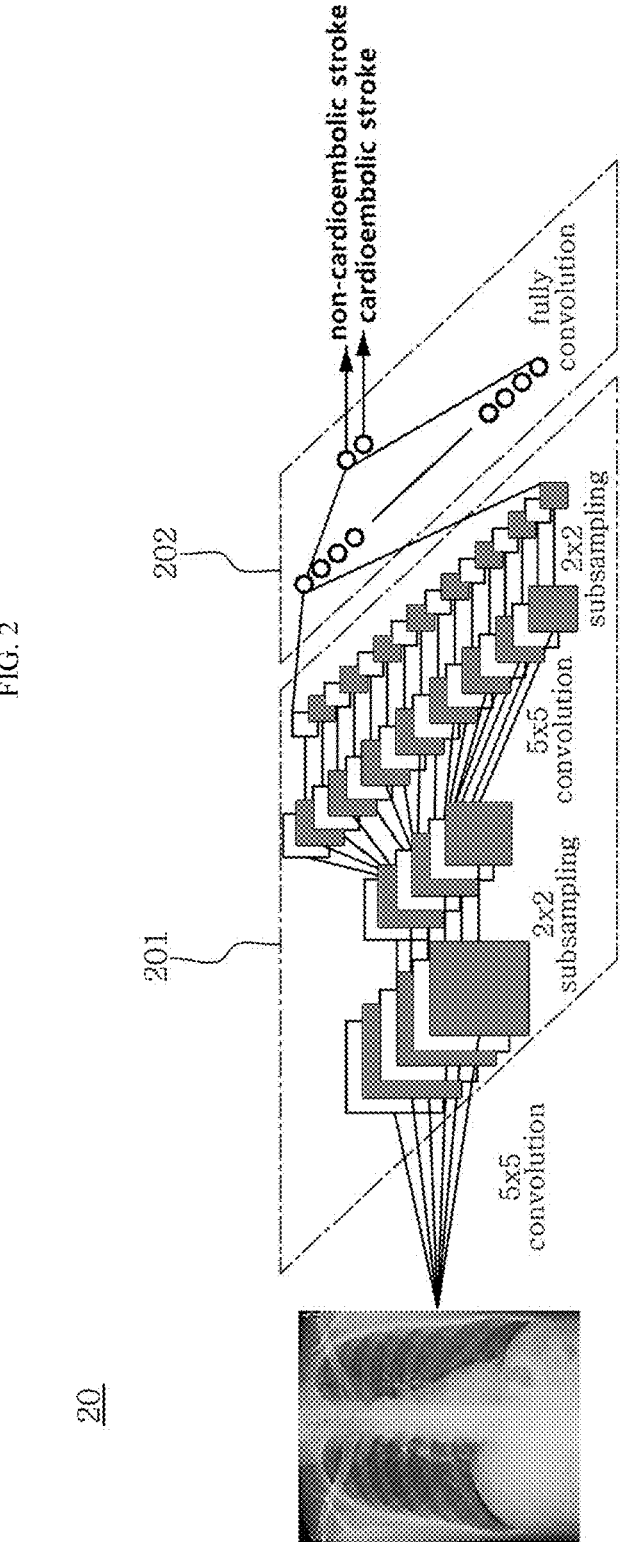
FIG. 2 is a diagram illustrating a layer of CNN structure according to an embodiment of the present invention.

FIG. 2 is a diagram showing a layer of a CNN structure that is a neural network model according to an embodiment of the present invention.

The neural network model is configured to extract features from the chest radiographic images to be classified of a subject, and determine whether the subject belongs to a group indicating cardioembolic stroke based on the extracted features.

In the present description, the neural network model may include a deep learning model, where the deep learning model may be in a form in which artificial neural networks are stacked in multiple layers. The deep learning model automatically learns the features of each image by learning a large amount of data in a deep neural network comprising multi-layer networks, and thereby trains a network in a way that minimizes an error in prediction accuracy, i.e., an objective function.

In the present description, the deep learning model may use, for example, convolutional neural network (CNN), deep hierarchical network (DHN), convolutional deep belief network (CDBN), deconvolutional deep network (DDN), etc., but may use various deep learning models currently or in the future. In the present description, a CNN-based deep learning model is used as an example, but the present invention is not limited thereto and may use various deep learning models currently or in the future.

Referring to FIG. 2, the deep learning technology used by the neural network model 20 of a method for assisting diagnosis of cardioembolic stroke using chest radiographic images may perform convolution and subsampling on the input chest radiographic images. The neural network model 20 includes a feature extraction part 201 for extracting features from chest radiographic images, and a classification part 202 that performs classification on the input chest radiographic images using a weight loss function for the extracted features.

In convolution, a feature map is created by using a plurality of filters for each region of chest radiographic images in a convolution layer. Subsampling or pooling reduces the size of a feature map in a subsampling layer to extract features of chest radiographic images that are invariant to changes in position or rotation.

The feature extraction part 201 may extract, from chest radiographic images, features of various levels from low-level features such as points, lines, and planes to complex and meaningful high-level features by repeating convolution and/or sub-sampling.

In the step S12, feature information related to diagnosis of stroke is extracted from the chest radiographic images to be classified of a subject by the feature extraction part 201. This extracted feature information may be used as auxiliary information for diagnosing cardioembolic stroke.

The features finally extracted from the feature extraction part 201 are input to the classification part 202.

The classification part 202 determines whether the subject has cardioembolic stroke based on the features finally extracted from the feature extraction part 201.

Figure 3:
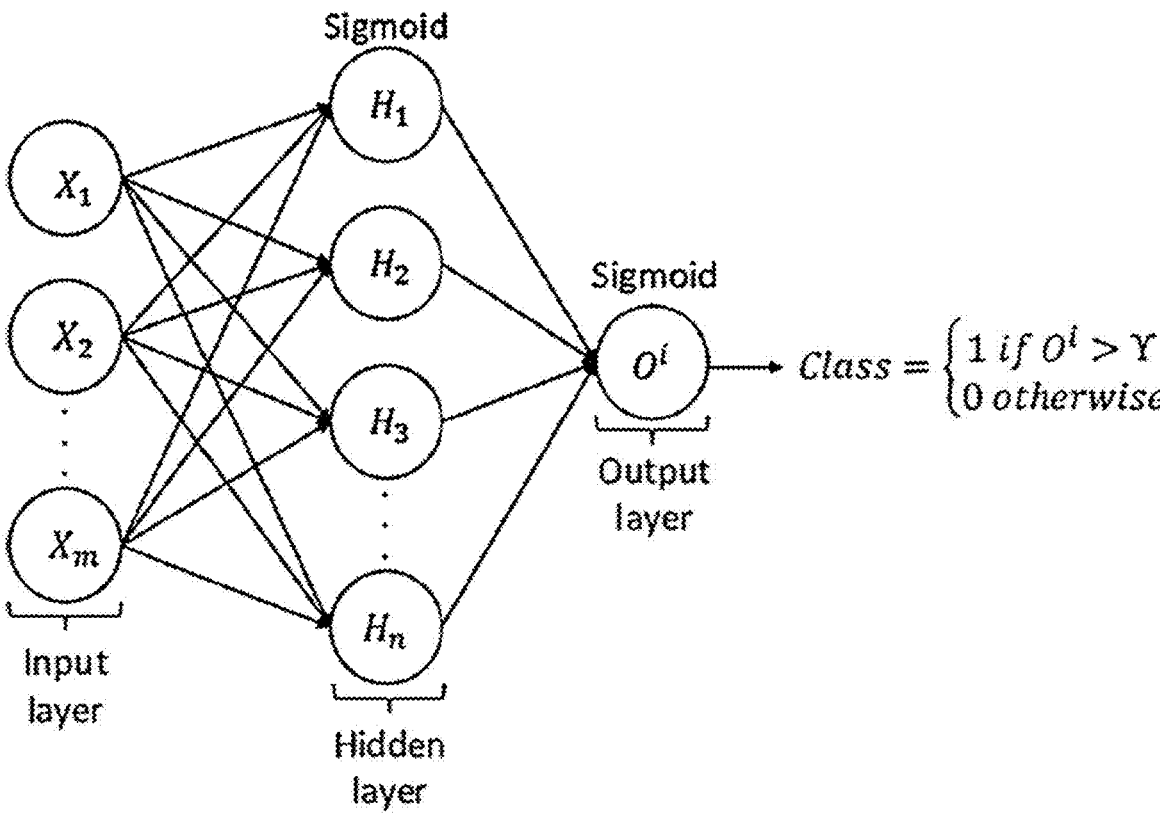
FIG. 3 is a diagram illustrating a sigmoid layer of a neural network model which can be used in determining cardioembolic stroke and non-cardioembolic stroke in an embodiment of the present invention.

FIG. 3 is a diagram showing a sigmoid layer usable in the classification part 202 of the deep learning neural network model 20 of FIG. 2 according to an embodiment of the present invention.

The neural network model of the present invention includes a fully connected layer, and the fully connected layer includes a single output sigmoid layer so that the neural network model learns classification into a cardioembolic stroke group and a non-cardioembolic stroke group. Sigmoid activation may be performed in the last fully connected layer to cause the output to have a range of [0, 1]. Existing DenseNet which is a structure that classifies 1000 labels is replaced with the single output sigmoid layer so that the neural network model learns classification into a cardioembolic stroke group (1) and a non-cardioembolic stroke group (0).

The neural network model 20 that determines cardioembolic stroke may have a DenseNet structure, but is not limited thereto. In addition to this, various neuronal network structures may be used, and in any case, the neuronal network may be defined to receive a specific chest radiographic image as an input and output a feature value corresponding to the probability of cardioembolic stroke.

The neural network model 20, which is a CNN-based deep learning model, aims for optimized learning of parameters present in each individual layer in the feature extraction part 201 and the classification part 202. In the neural network model 20, the order of data determines the value of the initial parameter. In the present invention, the parameter may include a parameter indicating one or more of atrial volume index, early diastolic bicuspid annular tissue velocity (E/e'), frequency of bicuspid and tricuspid valve diseases, and ventricular ejection fraction.

In an embodiment, the neural network model 20 is trained to classify chest radiographic images into a cardioembolic stroke group and a non-cardioembolic stroke group using a plurality of training samples, and each of the plurality of training samples may include chest radiographic images for training and label information of the chest radiographic images. The label information may include gender, age, other diseases, smoking status, and the like. The label information indicating the non-cardioembolic stroke group includes information indicating patent forman oval (PFO)-related stroke. The PFO-related stroke is generally classified as cardioembolic stroke, but it is classified as a non-cardioembolic stroke because it does not cause major structural abnormalities of the heart and does not show features in chest radiographic images.

As such, the neural network model 20 of an embodiment of the present invention may better diagnose cardioembolic stroke caused by atrial fibrillation, atrial flutter, etc., which cause significant structural abnormalities of the heart and have a high risk, rather than diseases with a relatively low risk, which shows the superiority of the neural network model 20.

On the other hand, the classification part 202 of the neural network model 20 performs imaging diagnosis using a weight loss function-based neural network model that focuses on increasing the sensitivity of imaging diagnosis or increasing the specificity of imaging diagnosis.

In medicine in general, concepts such as accuracy, sensitivity, and specificity are important criteria for imaging diagnosis in diagnostic test medicine or preventive medicine in particular.

As shown in Table 1, when the test result for cardioembolic stroke is positive and a patient has a disease, it is called true positive, and when the test result for cardioembolic stroke is positive and a patient does not have a disease, it is called false positive. When the result for cardioembolic stroke is negative and a patient has a disease, it is called a false negative, and when the result for cardioembolic stroke is negative and a patient does not have a disease, it is called true negative. The false positive and false negative which are diagnostic result errors are referred to as type I error and type II error, respectively.

TABLE 1

|  | Disease | No disease |
| --- | --- | --- |
| Tested positive | True positive | False positive |
| Test negative | False negative | True negative |

The accuracy, specificity, and sensitivity are shown in Equations 1 to 3:

$$accuracy = \frac{true\ positive + true\ negative}{true\ positive + true\ negative + flase\ positive + false\ negative} \quad \text{[Equation 1]}$$

$$specificity = \frac{true\ negative}{true\ negative + flase\ positive} \quad \text{[Equation 2]}$$

$$sensitivity = \frac{true\ positive}{true\ positive + flase\ nagative} \quad \text{[Equation 3]}$$

Conventional neural network models focus only on increasing the accuracy of imaging diagnosis, classifying whether or not a tissue has a disease for imaging diagnosis, and not focusing on increasing the sensitivity or specificity of imaging diagnosis.

However, reducing the above-mentioned type I and type II errors simultaneously is more meaningful for actual imaging diagnosis. Minimizing type I errors increases specificity, while minimizing type II errors increases sensitivity.

The neural network model 20 of an embodiment of the present invention may be used as a more reliable method for assisting the diagnosis since it has increased sensitivity and specificity as well as accuracy regarding the presence or absence of a disease in determining cardioembolic stroke using chest radiographic images.

Moreover, for patient treatment in imaging diagnosis, minimizing false-negative type II errors may be even more important than false-positive type I errors. This is because it is fatal to a patient with actual cardioembolic stroke when the treatment period for the disease is delayed or missed due to the error in imaging diagnosis result showing that there was no cardioembolic stroke in the imaging diagnosis, but the patient actually had the disease.

Therefore, in the classification part 202 of the neural network model 20 of embodiments of the present invention, imaging diagnosis may be performed using a weight loss function-based neural network model focused on increasing the sensitivity of chest radiographic images.

In embodiments of the present invention, the heart included in the chest radiographic images input by the trained neural network model 20 using a weight loss function is classified as one of cardioembolic stroke group and a non-cardioembolic stroke group.

The neural network model 20, for the purpose of classification into a cardioembolic stroke group and a non-cardioembolic stroke group, is trained to predict the probability of which group an input belongs to. During the learning process, model parameters are adjusted so that these predictions are as close as possible to ground-truth probabilities. For example, in the case of cardioembolic stroke, when the ground-truth probability is 1 but the prediction of the neural network model is 0.4, the model parameters should be adjusted so that the prediction of 0.4 can be closer to the ground-truth probability of 1. When the adjustment is as close as possible, the learning is completed.

Here, a scale for determining "close", i.e., a method for determining whether it is different, is needed. In the deep learning field, a weight loss function is defined for this purpose. Various weight loss functions may be used to achieve the above-mentioned learning objective of minimizing type I and type II errors. As mentioned above, for patient treatment in diagnostic tests, minimizing false-negative type II errors may be far more important than false-positive type I errors.

Referring to back FIG. 1, additionally, the method for assisting diagnosis of cardioembolic stroke may further include a step S14 of outputting CAM images through a Grad-CAM model based on at least one of the acquired chest radiographic images to be classified and the information generated from the neural network model in order to identify the region of the chest radiographic images that affects diagnosis performed by the neural network model.

Figure 4:
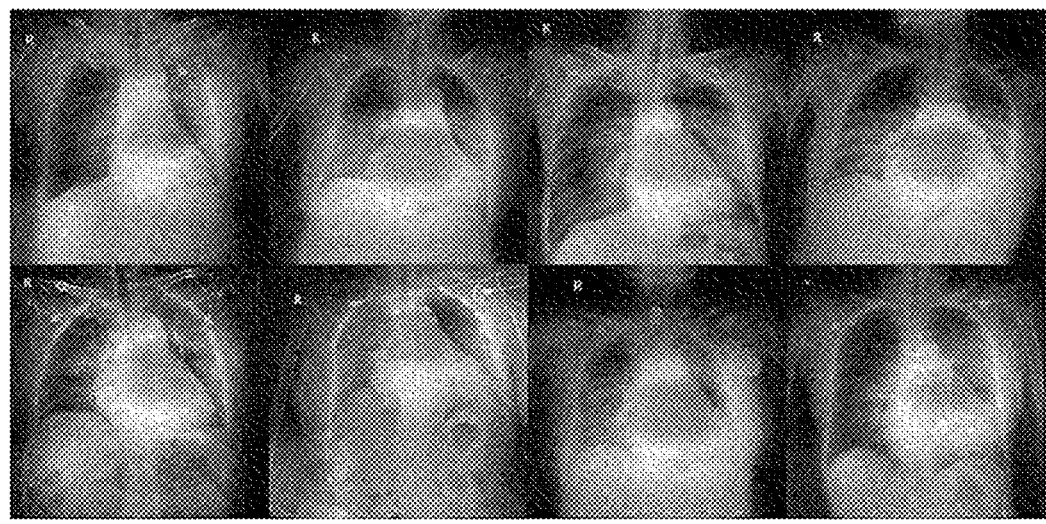
FIG. 4 is a diagram illustrating a step of outputting CAM images through Grad-CAM model to identify the region of the chest radiographic images that affects diagnosis performed by the neural network model in an embodiment of the present invention.

FIG. 4 is a diagram showing an output CAM image according to an embodiment of the present invention.

The step of outputting the CAM images may include obtaining a gradient class activation map (Grad-CAM), and outputting a CAM image based on the acquired activation map.

After classification is completed from the classification part 202 of the neural network model, the activity of each class is displayed as an image using an internal weight and a feature map, wherein the feature map refers to features created after performing a convolution operation on the image.

In an embodiment of the present invention, the method for obtaining the gradient class activation map (Grad-CAM) may be implemented by using the product of a gradient of the score (logit value) to be classified into a specific class for each grade and a feature map that has passed through convolution and the feature map that has passed through convolution.

The gradient class activation map (Grad-CAM) used in the embodiments of the present invention may overcome the disadvantage that the existing class activation map (CAM) structure cannot be used universally and may be used in almost all CNN structures. When the gradient class activation map (Grad-CAM) extracted in this way is changed to the original image in size and overlapped therewith, it may possible to identify which part of the original image was classified with a specific class.

As shown in FIG. 4, in the chest radiographic images belonging to a group indicative of having cardioembolic stroke, a suspected region including a region where left atrium is located is indicated by the Grad-CAM.

Experimental Example

In this experimental example, ASTRO-X refers to the CNN-based neural network model 20 of FIG. 2. CheXnet is a conventional deep learning model learned through the opinions of existing radiologists. DenseNet-121 was used for the ASTRO-X.

FIG. 5 is a table showing the reference characteristics of a study population according to an experimental example of the present invention.

Referring to FIG. 5, mRS refers to modified Rankin scale, BP is blood pressure, IV is intravenous, and LDL is low-density lipoprotein. Of the 4,064 cases of acute ischemic stroke diagnosed, 61% (n=2,478) were male, and the mean age was 68.7±12.6 years. Risk factors for these patients were hypertension [2,868 (70.6%)], diabetes [1,367 (33.6%)], and atrial fibrillation [919 (22.6%)]. The median of the national institute of health stroke scale (NIHSS) in the case of hospitalization is 3 [interquartile range (IQR): 1-7]. The average delay from symptom onset to diagnosis was 16.5 (IQR: 4.5-57.4) hours. 473 (11.6%) and 386 (9.5%) of patients underwent endovascular treatment and venous thrombolysis, respectively. A modified Rankin scale score of 0-2 was achieved after 3 months in 2,731 (67.2%) patients, with a mortality rate of 4.1%.

FIG. 6 is a table showing population characteristics of a learning data set based on echocardiography according to an experimental example of the present invention.

Referring to FIG. 6, echocardiography was performed in 80.3% (n=650) of the training data set. As a result of classification based on the characteristics of the study population according to the echocardiography, the correlation with other characteristics including the determination of cardioembolic stroke was not significant with a P-value of 0.05 or more.

FIGS. 7 to 12 are test results of ASTRO-X according to an experimental example of the present invention.

FIG. 7 is a table showing a comparison between results predicted by ASTRO-X, which is a model according to an experimental example of the present invention, and echocardiographic results.

In the table of FIG. 7, E/e' refers to a ratio of bicuspid inflow velocity to bicuspid annular early diastolic velocity, LV refers to the left ventricle, and * refers to a ratio of cardioembolic stroke (CE) to non-cardioembolic stroke (non-CE), which is calculated as mean and percentage for continuous and categorical variables. ** indicates moderate to severe severity.

Referring to FIG. 7, as a result of prediction by ASTRO-X for 650 test subjects, 163 persons were diagnosed with cardioembolic stroke, and 487 persons were diagnosed with non-cardioembolic stroke. According to the data from echocardiography, the correlation with other LA volume, LA volume index, LA AP diameter, E/e' etc. was significant with a P-value<0.01. That is, ASTRO-X using deep learning technology automatically learned the features of chest radiographic images to achieve the purpose of assisting diagnosis of cardioembolic stroke, but in particular, focused on the features of the left atrium and left ventricle.

FIG. 8 is a table showing the correlation between results from ASTRO-X of FIG. 7 and results from echocardiography results classified into true positive (TP), false positive (FP), false negative (FN), and true negative (TN).

Referring to FIG. 8, * indicates moderate to severe severity,  indicates analysis of variance for continuous variables and chi-square test categorical variables, LA refers to left atrium, AP refers to anteroposterior, LV refers to left ventricle, E/e' refers a ratio of bicuspid inflow velocity to bicuspid annular early diastolic velocity. In cases where cardioembolic stroke is predicted by STRO-X, it is shown that the cardiac ejection fraction is lower, the E/e' is higher, the volume index of left atrial and left ventricular is higher, and the probability of having regurgitation in the bicuspid valve is moderate to severe, which is higher than the cases where non-cardioembolic stroke is predicted. FIG. 8 like FIG. 7** also shows that ASTRO-X using deep learning technology automatically learns the features of chest radiographic images to achieve the purpose of assisting diagnosis of cardioembolic stroke, but in particular, focuses on the features of the left atrium and left ventricle.

FIG. 9 is a table comparing estimated causes of cardioembolic stroke based on predictions of ASTRO-X in FIG. 7. All percentages are calculated row by row, and * includes multiple embolic stroke and severe aortic stenosis with left atrial hypertrophy, which are classified as a high-risk cause based on the clinical reasoning of the attending physician.

Referring to FIG. 9, ASTRO-X was better in diagnosing cardioembolic stroke in the high-risk group than in the intermediate-risk group (P<0.01). Most of the causes of classification in the high-risk group were atrial fibrillation, and 75.3% of them were correctly classified as cardioembolic stroke. 91% of the intermediate-risk group were classified as non-cardioembolic stroke by ASTRO-X. Although PFO-related stroke is generally classified as cardioembolic stroke, it is classified as non-cardioembolic stroke because it does not cause major structural abnormalities of the heart and does not show any features in chest radiographic images. That is, ASTRO-X has the ability to better diagnose cardioembolic stroke caused by high-risk atrial fibrillation and atrial flutter, which cause significant structural abnormalities of the heart, rather than diseases with a relatively low risk.

Figure 10A:
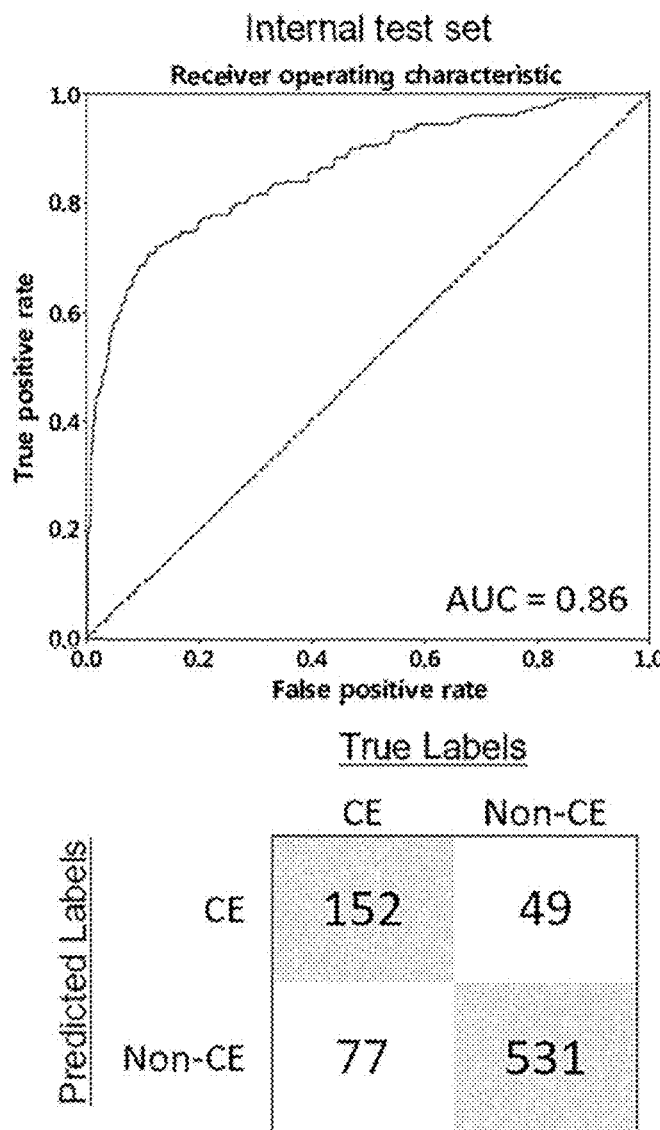
FIGS. 10A, 10B and 10C are diagrams relatively evaluating the performance of ASTRO-X according to an embodiment of the present invention by sensitivity, specificity, and accuracy.
Figures 10B, 10C:
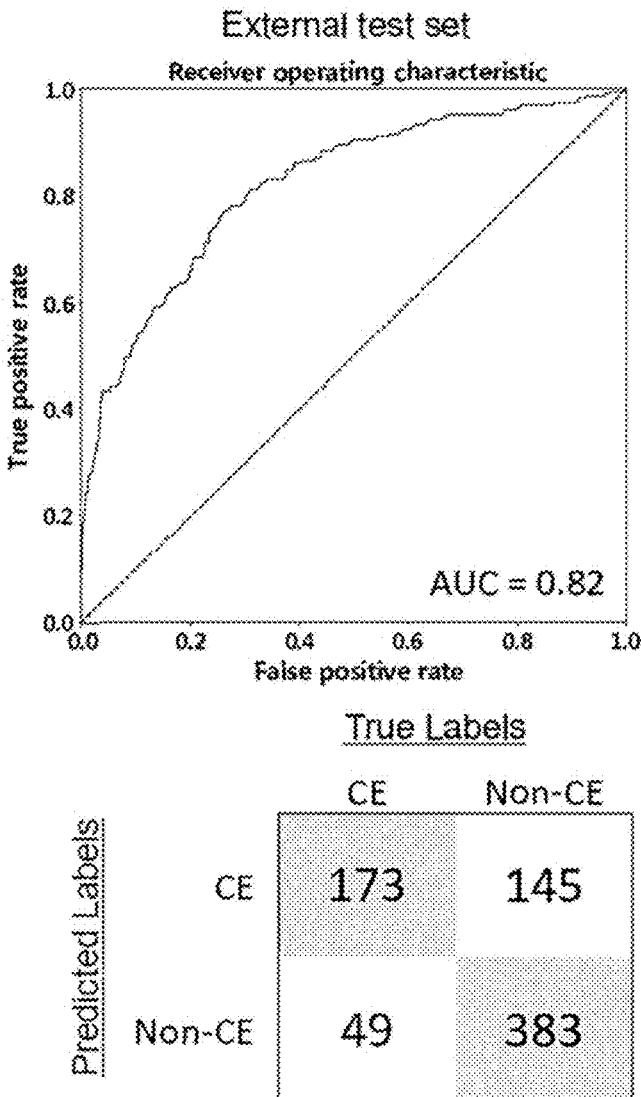

FIGS. 10A, 10B, and 10C are diagrams relatively evaluating the performance of ASTRO-X according to the experimental example by sensitivity, specificity, and accuracy.

FIGS. 10A and 10B show that some of the acquired chest radiographic images were divided into an internal test set and an external test set, and then the criteria for embolism change were first established from the internal data set.

Referring to FIG. 10C, the detection performance for each change pattern may be statistically analyzed by calculating the area under the curve (AUC). As a result, for the internal data set, AUC=0.86, sensitivity=0.66, and specificity=0.92, accuracy=0.84, and for the external data set, AUC=0.82, sensitivity=0.78, specificity=0.73, accuracy=0.74, which showed high reliability.

Therefore, the neural network model 20 of the embodiments of the present invention may be used as a more reliable method for assisting the diagnosis by increasing sensitivity and specificity as well as accuracy in determining cardioembolic stroke using chest radiographic images.

FIGS. 11A to 11D are CAM images of a patient with cardioembolic stroke according to an embodiment of the present invention.

Figure 11A:
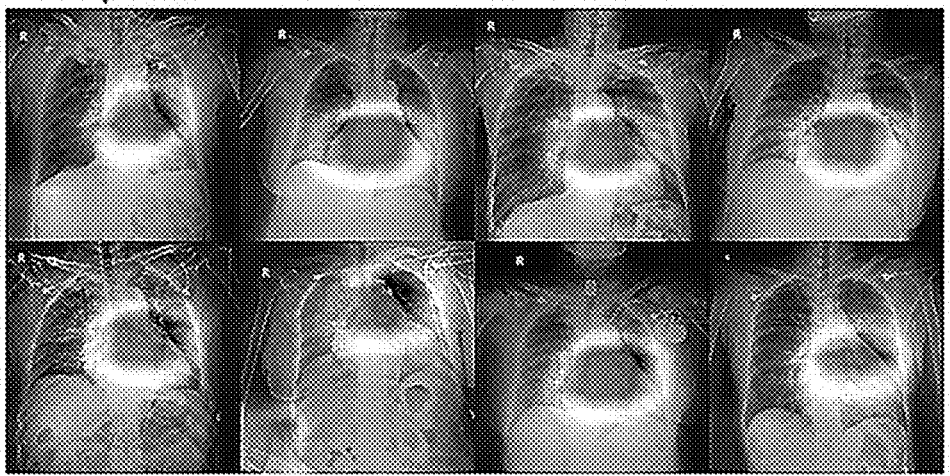
FIGS. 11A to 11D are images showing that the embolus is biased toward the left atrium in the case of cardioembolic stroke positive through Grad-CAM according to an embodiment of the present invention.
Figure 11B:
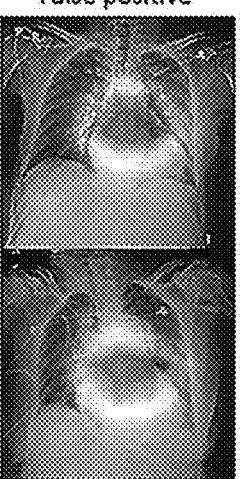
Figure 11C:
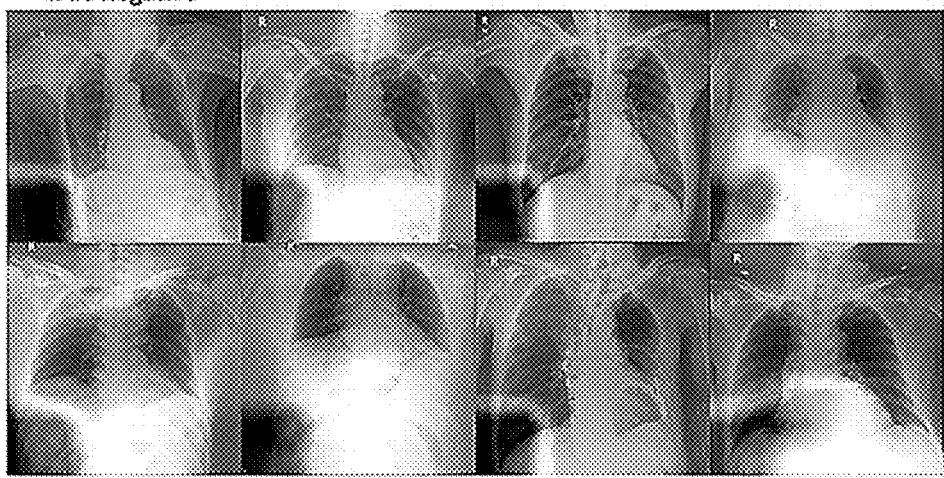
Figure 11D:
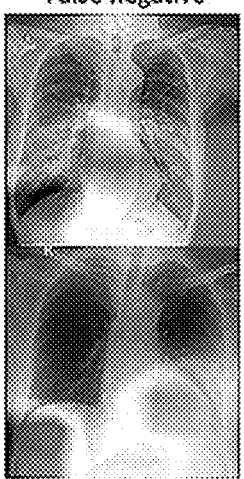

As shown in FIG. 11A, for true positive cases, when applying chest radiographic images to be classified belonging to a group indicative of having cardioembolic stroke to a Grad-CAM model, a CAM image showing the suspected region including the region where the left atrium is located may be obtained. In other words, it may be confirmed that the region where the left atrium is located has an effect on determining true positivity.

Figure 12:
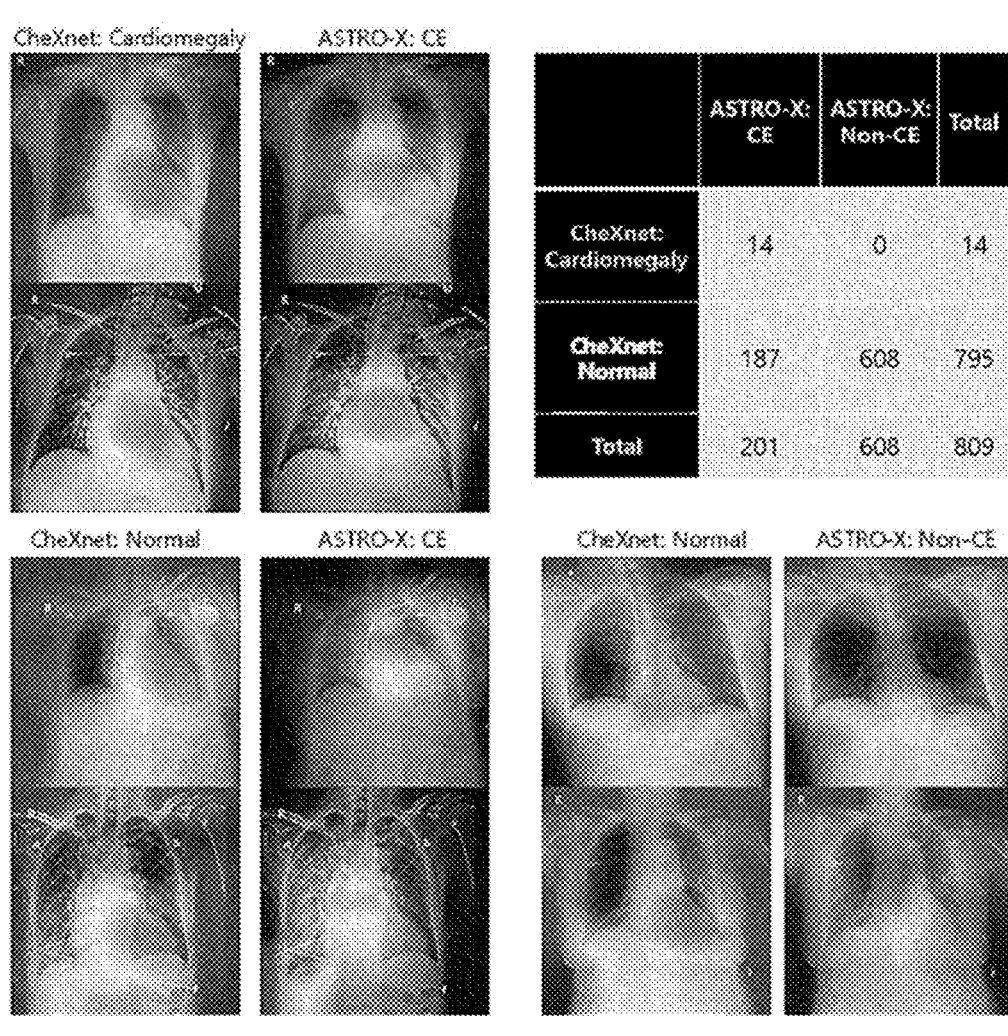
FIG. 12 compares the determination results of cardioembolic stroke using ASTRO-X and the determination results of cardiomegaly using CheXnet, according to an embodiment of the present invention.

According to an embodiment of the present invention, FIG. 12 compares the determination results of cardioembolic stroke according to ASTRO-X and the determination result of cardiac hypertrophy according to CheXnet.

Referring to FIG. 12, when a patient is diagnosed with cardioembolic stroke by ASTRO-X but diagnosed as normal by CheXnet, the effect of the present invention appears.

As shown in the CAM image, the suspected region of ASTRO-X was displayed as a narrower region than that of CheXnet. This is because, for CheXnet, the cardiomegaly score focusing on the contour of the entire heart is the main diagnostic criterion.

Therefore, it is confirmed that the neural network model 20 of FIG. 2 is suitable for learning, mainly focusing on the left atrium.

The above-described method for assisting diagnosis of cardioembolic stroke using chest radiographic images may be implemented by an apparatus, and the apparatus may be executed by a computing device including at least a part of a processor, memory, user input device, and presentation device. The memory is a medium that stores computer-readable software, applications, program modules, routines, instructions, and/or data that are coded to perform specific tasks when executed by the processor. The processor may read and execute computer-readable software, applications, program modules, routines, instructions, and/or data stored in the memory. The user input device may allow a user to input commands that cause the processor to perform specific tasks and to input data needed to perform specific tasks. The user input device may include a physical or virtual keyboard or keypad, key buttons, mouse, joystick, trackball, touch-sensitive input means, or microphone. The presentation device may include a display, a printer, a speaker, or a vibrator and the like.

The computing device may include a variety of devices such as a smart phone, a tablet, a laptop, a desktop, a server, a client, and the like. The computing device may include a single stand-alone device or multiple computing devices operating in a distributed environment consisting of multiple computing devices cooperating with each other through a communication network.

In addition, the above-mentioned imaging diagnosis method may be executed by a computing device provided with a processor, and, when executed by the processor, memory storing computer readable software, applications, program modules, routines, instructions, and/or data structures, etc. coded to perform a method for assisting diagnosis of cardioembolic stroke using chest radiographic images.

The embodiments described above may be implemented through various means. For example, the embodiments may be implemented by hardware, firmware, software, or a combination thereof.

When executed by hardware, the method for assisting diagnosis of cardioembolic stroke using chest radiographic images may be implemented by one or more of application specific integrated circuits (AS ICs), digital signal processors (DSPs), digital signal processing devices (DSPDs), programmable logic devices (PLDs), field programmable gate arrays (FPGAs), processors, controllers, microcontrollers or microprocessors, etc.

For example, the method for assisting diagnosis of cardioembolic stroke using chest radiographic images according to embodiments may be implemented using an artificial intelligence semiconductor device in which neurons and synapses of a deep neural network are implemented as semiconductor devices.

The semiconductor devices may include currently used semiconductor devices such as SRAM, DRAM, NAND, etc., next-generation semiconductor devices, such as RRA, STT MRAM, PRAM, etc., or a combination thereof.

When the method for assisting diagnosis of cardioembolic stroke using chest radiographic images according to embodiments is implemented using an artificial intelligence semiconductor device, the results (weights) of learning the neural network model as software may be transferred to synaptic mimic devices arranged in an array or learning may be carried out in the artificial intelligence semiconductor device.

When executed by firmware or software, the method for assisting diagnosis of cardioembolic stroke using chest radiographic images may be implemented in the form of a function, a procedure, apparatus that performs the functions or operations described above. The software code may be stored in a memory unit and run by the processor. The memory unit may be located inside or outside the processor and exchange data with the processor by various means known in the art.

In addition, the terms such as "system", "processor", "controller", "component", "module", "interface", "model", or "unit" generally refer to a computer-related entity hardware, a combination of hardware and software, software, or running software. For example, the aforementioned components may be, but are not limited to, a process driven by a processor, a processor, a controller, a control processor, an object, a thread of execution, a program, and/or a computer. For example, all of the application running on the controller or processor and the controller or processor may be components. One or more components may be within the process and/or thread of execution, and the components may be located on one machine (e.g., system, computing device, etc.) or distributed across two or more machines.

The above description is merely an illustrative example of the technical idea of the present invention, and those skilled in the art can make various modifications and variations without departing from the essential characteristics of the technical idea. In addition, since the present embodiments are not intended to limit the technical idea of the present invention but to explain, the scope of the present technical idea is not limited by these embodiments. The scope of protection of the present invention should be construed by the claims below, and all technical ideas within the scope equivalent thereto should be construed as being included in the scope of the rights of the present invention.

INDUSTRIAL APPLICABILITY

An apparatus and a method for assisting diagnosis of cardioembolic stroke using chest radiographic images of the present invention may help diagnose cardioembolic stroke using chest radiographic images that could be taken simply and inexpensively.

What is claimed is:

1. A method for assisting diagnosis of cardioembolic stroke, in which the method is performed by a processor and is to assist diagnosis of cardioembolic stroke by using chest radiographic images, comprising:
acquiring chest radiographic images to be classified of a subject;
and generating cardioembolic stroke auxiliary information from the chest radiographic images to be classified of the subject by using a neural network model;
wherein the neural network model is configured to extract features from the chest radiographic images to be classified of the subject, and determine, based on the extracted features, whether the subject belongs to a group indicative of having cardioembolic stroke,

wherein the neural network model is trained, using a plurality of training samples, to classify chest radiographic images into a cardioembolic stroke group and a non-cardioembolic stroke group, and
wherein each of the plurality of training samples includes a chest radiographic image for training and label information thereof.

2. The method for assisting diagnosis of cardioembolic stroke of claim 1,
wherein the neural network model has a convolutional neural network (CNN) structure.

3. The method for assisting diagnosis of cardioembolic stroke of claim 2,
wherein the neural network model is learned by adjusting parameters, wherein the parameters include parameters indicating one or more of left atrial volume index, early diastolic bicuspid annular tissue velocity (E/e'), frequency of bicuspid and tricuspid valve disease, and left ventricular ejection fraction, and
wherein the left atrial volume index, the E/e', and the left ventricular ejection fraction are correlated with structural abnormalities of a left atrium that are indicative of cardioembolic stroke.

4. The method for assisting diagnosis of cardioembolic stroke of claim 3,
wherein the neural network model includes a fully connected layer,
wherein the fully connected layer includes a single output sigmoid layer so that the neural network model learns classification into a cardioembolic stroke group and a non-cardioembolic stroke group.

5. The method for assisting diagnosis of cardioembolic stroke of claim 1,
further comprising outputting class activation map (CAM) CAM images through a gradient class activation map (Grad-CAM) model based on at least one of the acquired chest radiographic images to be classified and the information generated from the neural network model in order to identify the region of the chest radiographic images that affects diagnosis performed by the neural network model.

6. The method for assisting diagnosis of cardioembolic stroke of claim 5,
wherein a suspected region including the region where the left atrium is located is indicated, by the Grad-CAM, in chest radiographic images to be classified that belong to a group indicative of having cardioembolic stroke,
and wherein the region where the left atrium is located is identified based on structural features of left atrial enlargement that are characteristic of cardioembolic stroke.

7. A non-transitory computer-readable recording medium readable by a computer and storing program instructions operable by the computer, which causes a processor of the computer to perform the method for assisting diagnosis of cardioembolic stroke according to claim 1 when the program instructions are executed by the processor.

8. An apparatus for assisting diagnosis of cardioembolic stroke, the apparatus comprising a processor and memory and being configured to perform operations comprising:
acquiring chest radiographic images to be classified of a subject; and generating, using a neural network model, auxiliary information for diagnosis of cardioembolic stroke from the chest radiographic image to be classified of the subject;
wherein the neural network model is configured to extract features from the chest radiographic images to be classified of the subject, and determine, based on the extracted features, whether the subject belongs to a group indicative of having cardioembolic stroke, wherein the neural network model is trained, using a plurality of training samples, to classify chest radiographic images into a cardioembolic stroke group and a non-cardioembolic stroke group, and wherein each of the plurality of training samples includes a chest radiographic image for training and label information thereof.

9. The apparatus for assisting diagnosis of cardioembolic stroke of claim 8, wherein the neural network model has a convolutional neural network (CNN) structure.

10. The apparatus for assisting diagnosis of cardioembolic stroke of claim 9, wherein the neural network model is learned by adjusting parameters, wherein the parameters include parameters indicating one or more of left atrial volume index, early diastolic bicuspid annular tissue velocity (E/e'), frequency of bicuspid and tricuspid valve disease, and left ventricular ejection fraction, and wherein the left atrial volume index, the E/e', and the left ventricular ejection fraction are correlated with structural abnormalities of a left atrium that are indicative of cardioembolic stroke.

11. The apparatus for assisting diagnosis of cardioembolic stroke of claim 10, wherein the neural network model includes a fully connected layer, wherein the fully connected layer includes a single output sigmoid layer so that the neural network model learns classification into a cardioembolic stroke group and a non-cardioembolic stroke group.

12. The apparatus for assisting diagnosis of cardioembolic stroke of claim 8, wherein the operations further comprise outputting class activation map (CAM) images through a gradient class activation map (Grad-CAM) model based on at least one of the acquired chest radiographic images to be classified and the information generated from the neural network model in order to identify the region of the chest radiographic images that affects diagnosis performed by the neural network model.

13. The apparatus for assisting diagnosis of cardioembolic stroke of claim 12, wherein a suspected region including the region where the left atrium is located is indicated, by the Grad-CAM, in chest radiographic images to be classified that belong to a group indicative of having cardioembolic stroke, and wherein the region where the left atrium is located is identified based on structural features of left atrial enlargement that are characteristic of cardioembolic stroke.

* * * * *